(12) United States Patent
Yoshimoto et al.

(10) Patent No.: US 8,700,349 B2
(45) Date of Patent: Apr. 15, 2014

(54) METHOD FOR MEASURING SCATTERING ABSORBER AND DEVICE FOR MEASURING SCATTERING ABSORBER

(75) Inventors: Kenji Yoshimoto, Hamamatsu (JP); Kazuyoshi Ohta, Iwata (JP); Daisuke Yamashita, Hamamatsu (JP); Hiroaki Suzuki, Hamamatsu (JP)

(73) Assignee: Hamamatsu Photonics K.K., Hamamatsu-shi, Shizuoka (JP)

(*) Notice: Subject to any disclaimer, the term of this patent is extended or adjusted under 35 U.S.C. 154(b) by 404 days.

(21) Appl. No.: 13/130,117

(22) PCT Filed: Sep. 1, 2009

(86) PCT No.: PCT/JP2009/065239
§ 371 (c)(1),
(2), (4) Date: May 19, 2011

(87) PCT Pub. No.: WO2010/061673
PCT Pub. Date: Jun. 3, 2010

(65) Prior Publication Data
US 2011/0224931 A1    Sep. 15, 2011

(30) Foreign Application Priority Data
Nov. 25, 2008  (JP) .................... 2008-299803

(51) Int. Cl.
*G01R 13/02*    (2006.01)
*G06F 19/00*    (2011.01)
*A61B 5/00*    (2006.01)
*G01N 21/47*    (2006.01)

(52) U.S. Cl.
CPC ............. *A61B 5/0091* (2013.01); *A61B 5/4312* (2013.01); *G01N 21/4795* (2013.01); *A61B 5/0059* (2013.01)

USPC ............................................. 702/71; 356/432

(58) Field of Classification Search
CPC .. A61B 5/0091; A61B 5/4312; A61B 5/0059; A61B 5/14; A61B 5/1455; G01N 21/4795
USPC ............. 702/66, 67, 70, 71, 73, 74, 147, 189; 356/338, 432
See application file for complete search history.

(56) References Cited

U.S. PATENT DOCUMENTS 6,567,165 B1 * 5/2003 Tsuchiya et al. ............... 356/338
6,704,110 B2 * 3/2004 Tsuchiya ...................... 356/432

FOREIGN PATENT DOCUMENTS

JP    10-111238    4/1998
JP    10-148611    6/1998

(Continued)

*Primary Examiner* — John H Le
(74) *Attorney, Agent, or Firm* — Drinker Biddle & Reath LLP (57) ABSTRACT

In a method for measuring a scattering medium, pulse light with a predetermined wavelength is made incident on a scattering medium which is a measurement object and a scattering medium for reference, the pulse light transmitted inside the scattering media is detected to acquire a light detection signal, the measurement waveform is acquired on the basis of the detected light detection signal, a parameter of a function showing the theoretical waveform of the measurement object is specified in such a manner that the result of convolution operation on the theoretical waveform of the measurement object and the measurement waveform of the reference is made equal to the result of convolution operation on the theoretical waveform of the reference and the measurement waveform of the measurement object, and calculation is made for the internal information of the scattering medium on the basis of the theoretical waveform shown by the function.

3 Claims, 7 Drawing Sheets

(56) References Cited

FOREIGN PATENT DOCUMENTS

| JP | 2000-146828 | 5/2000 |
| JP | 2001-004533 | 1/2001 |
| JP | 2002-139420 | 5/2002 |
| JP | 2008-2908 | 1/2008 |

* cited by examiner

METHOD FOR MEASURING SCATTERING ABSORBER AND DEVICE FOR MEASURING SCATTERING ABSORBER

TECHNICAL FIELD

The present invention relates to a method for measuring a scattering medium and an apparatus for measuring a scattering medium in order to measure the internal information of scattering media such as a living body, etc.

BACKGROUND ART

As an apparatus for measuring the internal information of a scattering medium such as a living body, an apparatus which uses pulse light transmitted inside the scattering medium, for example, an apparatus for measuring a scattering medium by using time resolved spectroscopy (TRS) such as an optical mammography apparatus is available. A time-resolved waveform of light measured by the above-described apparatus includes not only response time characteristics of a scattering medium which is a measurement object but also response time characteristics (instrumental function) of the apparatus itself. Therefore, in carrying out an analysis of data, it is necessary to eliminate the influence of the instrumental function from a measurement waveform, that is, to correct the data.

In existing optical mammography apparatuses, actually measured instrumental functions are used to correct data. When measuring an instrumental function, it is necessary to remove many optical fibers for irradiation and detection installed on a gantry unit, fix a module for measuring the instrumental function in place of the optical fibers and install the optical fibers on the gantry unit again after completion of measurement of the instrumental function. Therefore, this method poses a problem that prolongs the working time and measurement time.

In order to solve the above problem, a method described in Patent Literature 1 by which a measurement waveform of a scattering medium which is a measurement object is corrected without using an instrumental function has been proposed. According to this method, the measurement waveform of the scattering medium which is the measurement object, a measurement waveform of a scattering medium for reference with known optical coefficients (an absorption coefficient and a scattering coefficient) and the theoretical waveform thereof are used to correct the measurement waveform of the scattering medium which is the measurement object. Thereby, it is possible to acquire the internal information of the scattering medium more easily, with the influence of the instrumental function taken into account.

CITATION LIST

Patent Literature

[Patent Literature 1] Japanese Published Unexamined Patent Application No. 2008-2908

SUMMARY OF INVENTION

Technical Problem

However, when the method described in Patent Literature 1 is used, there is a case where, due to the influence of noise contained in a measurement waveform on correction, the waveform after processing is greatly deformed. The deformed waveform after processing will influence the correctness of the internal information calculated subsequently. In view of the above-described situation, a method for acquiring the internal information of the scattering medium more accurately and easily, with the instrumental function taken into account, even where noise is contained in the measurement waveform has been demanded.

The present invention has been made for solving the above problem, an object of which is to provide a method for measuring a scattering medium and an apparatus for measuring a scattering medium capable of acquiring the internal information of the scattering medium more accurately and easily, with an instrumental function taken into account, even where noise is contained in a measurement waveform.

Solution to Problem

In order to attain the above object, a method for measuring a scattering medium in the present invention includes a light incident step in which pulse light with a predetermined wavelength is made incident from a light incident position to a scattering medium which is a measurement object and a scattering medium for reference, a light detecting step in which the pulse light made incident in the light incident step and transmitted inside each of the scattering media is detected at a light detecting position to acquire a light detection signal, a signal processing step in which a measurement waveform showing temporal change in light intensity is acquired on the basis of the light detection signal detected in the light detecting step, a waveform processing step in which when the measurement waveform of the scattering medium which is the measurement object acquired in the signal processing step is given as $P_m(t)$, the theoretical waveform of the scattering medium which is the measurement object expressed by a previously available function having a predetermined parameter is given as $P_m^{theory}(t)$, the measurement waveform of the scattering medium for reference acquired in the signal processing step is given as $P_r(t)$, the theoretical waveform of the previously available scattering medium for reference is given as $P_r^{theory}(t)$ and convolution is given as an operator "*", the parameter is specified on the basis of the following formula;

$$P_r*(t)P_m^{theory}(t) = P_m(t)*P_r^{theory}(t) \quad \text{[mathematical formula 1]}$$

and, an internal information calculation step in which on the basis of the theoretical waveform of the scattering medium which is the measurement object expressed by the function having the specified parameter in the waveform processing step, calculation is made for the internal information of the scattering medium which is the measurement object.

A measurement waveform of a scattering medium which is a measurement object and that of a scattering medium for reference are influenced by an instrumental function. Therefore, the parameter is specified on the basis of the above-described relationship of waveforms, by which it is possible to acquire a theoretical waveform in which the influence of an instrumental function is eliminated from the measurement waveform of the scattering medium which is the measurement object, without using the instrumental function. Further, the theoretical waveform of the scattering medium which is the measurement object is given as a previously available function with a predetermined parameter, thus making it possible to prevent the influence of variance in measurement waveform. That is, even where noise is contained in the measurement waveform, it is possible to obtain the theoretical waveform of the scattering medium which is the measurement object more accurately. Therefore, according to the present invention, even where noise is contained in a measurement waveform, it is possible to acquire the internal information of a scattering medium more accurately and easily, with an instrumental function taken into account.

A function showing $P_m^{theory}(t)$ is a function of discrete time $t_n$ and, when A, α, β are given as parameters, c is given as a value showing the speed of light, and γ is given as a value showing a distance between a light incident position and a light detecting position, the function is desirably expressed by the following formula;

[Mathematical formula 2]

$$P_m^{theory}(t_n) = A \cdot t_n^{-\frac{5}{2}} \cdot \exp(-\alpha c t_n) \cdot \exp\left(-\frac{\gamma^2 + \kappa^2}{4\xi c t_n}\right)$$

(here,

[mathematical formula 3]

$$\xi = \frac{1}{3\beta}, \kappa = \frac{1}{\beta}.)$$

The above function shows light transmitted inside a scattering medium more properly. Thus, it is possible to obtain a theoretical waveform of a scattering medium which is a measurement object more accurately. As a result, it is also possible to acquire the internal information of the scattering medium more accurately.

Moreover, the present invention can be described not only as an invention related to a method for measuring a scattering medium, as described above, but also as an apparatus for measuring a scattering medium, as will be described below. The latter is only different in category, and these two inventions are practically the same and have similar actions and effects.

That is, an apparatus for measuring a scattering medium in the present invention includes light incident means in which pulse light with a predetermined wavelength is made incident from a light incident position to a scattering medium which is a measurement object and a scattering medium for reference, light detecting means in which the pulse light made incident in the light incident means and transmitted inside each of the scattering media is detected at a light detecting position to acquire a light detection signal, signal processing means in which a measurement waveform showing temporal change in light intensity is acquired on the basis of the light detection signal detected by the light detecting means, waveform processing means in which when the measurement waveform of the scattering medium which is the measurement object acquired by the signal processing means is given as $P_m(t)$, the theoretical waveform of the scattering medium which is the measurement object expressed by a previously available function having a predetermined parameter is given as $P_m^{theory}(t)$, the measurement waveform of the scattering medium for reference acquired by the signal processing means is given as $P_r(t)$, the theoretical waveform of the previously available scattering medium for reference is given as $P_r^{theory}(t)$ and convolution is given as an operator "*", the parameter is specified on the basis of the following formula, $$P_r(t)*P_m^{theory}(t)=P_m(t)*P_r^{theory}(t) \quad \text{[Mathematical formula 4]}$$

and, internal information calculation means in which on the basis of the theoretical waveform of the scattering medium which is the measurement object expressed by the function having the specified parameter by the waveform processing means, calculation is made for the internal information of the scattering medium which is the measurement object.

Advantageous Effects of Invention

According to the present invention, it is possible to acquire a theoretical waveform in which the influence of an instrumental function is eliminated from a measurement waveform of a scattering medium which is a measurement object without using the instrumental function. Further, the theoretical waveform of the scattering medium which is the measurement object is given as a previously available function with a predetermined parameter. Thereby, even where noise is contained in the measurement waveform, it is possible to obtain the theoretical waveform of the scattering medium which is the measurement object more accurately. Therefore, according to the present invention, even where noise is contained in the measurement waveform, it is possible to acquire the internal information of the scattering medium more accurately and easily, with the influence of an instrumental function taken into account.

DESCRIPTION OF EMBODIMENTS

Hereinafter, a detailed description will be made for a preferred embodiment of the method for measuring a scattering medium and the apparatus for measuring a scattering medium in the present invention by referring to the drawings. In description of the drawings, the same components are given the same reference numerals, and overlapping description will be omitted. It is noted that the dimensional ratio given in the drawings is not necessarily in agreement with that referred to in the description.

Figure 1:
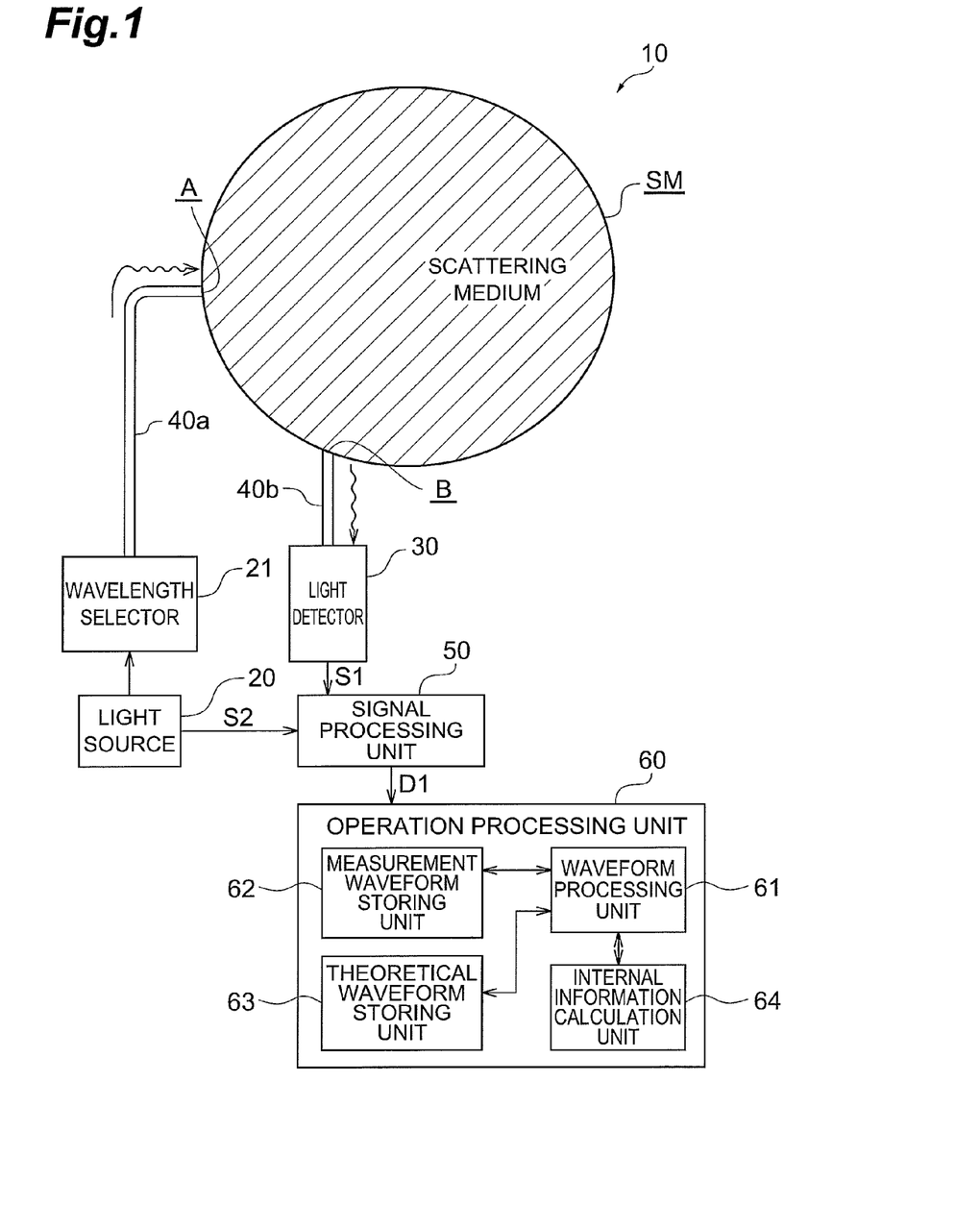
FIG. 1 is a drawing which shows a functional configuration of an apparatus for measuring a scattering medium in an embodiment of the present invention.
Figure 2:
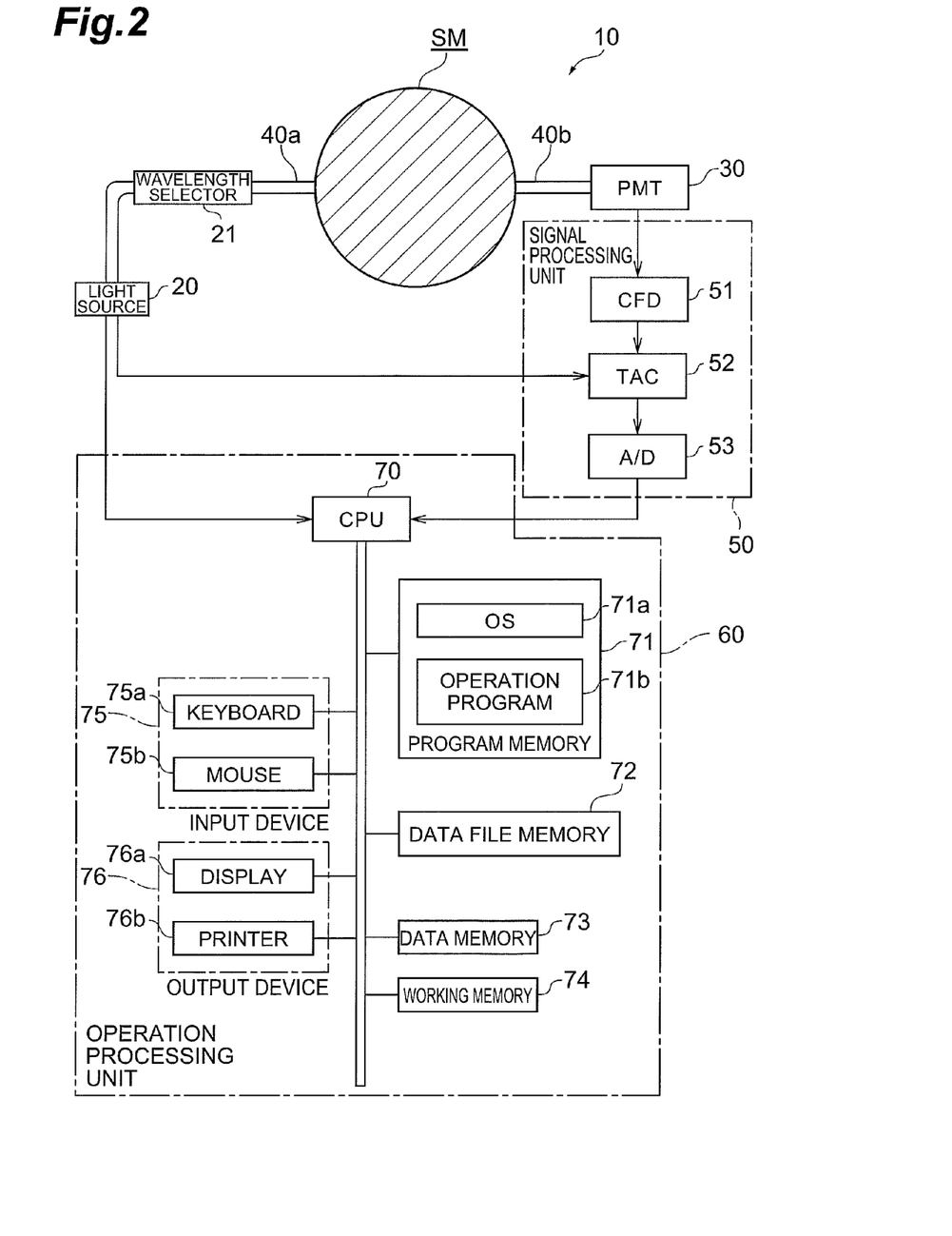
FIG. 2 is a drawing which shows a hardware configuration of the apparatus for measuring a scattering medium of the embodiment in the present invention.

FIG. 1 shows a functional configuration of an apparatus 10 for measuring a scattering medium of the present embodiment. FIG. 2 shows a hardware configuration of the apparatus 10 for measuring a scattering medium of the present embodiment. The apparatus 10 for measuring a scattering medium is an apparatus for measuring the internal information of a scattering medium. A scattering medium which is a measurement object of the apparatus 10 for measuring a scattering medium is to scatter and absorb light made incident on itself, for example, a living body. Further, the internal information to be measured is, for example, a scattering coefficient of the scattering medium, an absorption coefficient thereof and concentrations of respective components contained in the scattering medium. The apparatus 10 for measuring a scattering medium in the present embodiment is applied, for example, to the diagnosis of breast cancer by measuring the internal information of these matters. The hardware configuration shown in FIG. 2 is a configuration for carrying out a high-speed time waveform measurement method by using a so-called time correlation single photon measurement method.

As shown in FIG. 1 and FIG. 2, the apparatus 10 for measuring a scattering medium is provided as a component with a light source 20, a wavelength selector 21, a light detector 30, a light guide for light incidence 40$a$, a light guide for light detection 40$b$, a signal processing unit 50, and an operation processing unit 60.

The light source 20 is a device for generating pulse light with a predetermined wavelength for making the light incident on a scattering medium SM. As the pulse light which is generated by the light source 20 and made incident on the scattering medium SM, pulse light which is short in time width sufficient for measuring the internal information of the scattering medium SM is used. Normally, time width which is 1 ns or less is selected. The pulse light generated from the light source 20 is input into the wavelength selector 21. Various substances such as a light emitting diode, a laser diode, and various types of pulse diodes may be used as the light source 20.

The wavelength selector 21 is a device for selecting pulse light with a predetermined wavelength out of the pulse light input from the light source 20 according to a wavelength thereof. The pulse light generated by the light source 20 and selected by the wavelength selector 21 according to a wavelength can be selected appropriately depending on a scattering medium SM which is a measurement object. However, in general, for example, in a living body, in view of a relationship between a penetration efficiency of the living body and a spectral absorption coefficient of an absorbing component to be determined, etc., a wavelength of about 700 to 900 nm in a near-infrared ray region is used. The pulse light selected by the wavelength selector 21 according to a wavelength is input into an input terminal of the light guide for light incidence 40$a$. Where the internal information is measured for a plurality of components or in other cases, the light source 20 and the wavelength selector 21 are configured if necessary in such a manner that pulse light of a plurality of wavelength components can be made incident as measured light. Further, where it is not necessary to make wavelength selection or in other cases, wavelength selector 21 may not be installed.

The light guide for light incidence 40$a$ is to accept the input of pulse light at the input terminal thereof from the wavelength selector 21, thereby making the pulse light incident on a scattering medium SM from the output terminal thereof. The light guide for light incidence 40$a$ is installed in such a manner that the output terminal is positioned at a light incident position A on the surface of the scattering medium SM. More specifically, the light guide for light incidence 40$a$ is configured with an optical fiber capable of sending pulse light. The above-described light source 20, the wavelength selector 21 and the light guide for light incidence 40$a$ compose light incident means for making incident pulse light with a predetermined wavelength from the light incident position A to the scattering medium SM.

The light guide for light detection 40$b$ is to input light transmitted inside a scattering medium SM at the input terminal thereof, thereby outputting the light to the light detector 30 from the output terminal thereof. The light guide for light detection 40$b$ is installed in such a manner that the input terminal is positioned on a light detecting position B on the surface of the scattering medium SM. More specifically, the light guide for light detection 40$b$ is configured with an optical fiber capable of sending light.

The light detector 30 is a device for detecting light input from the light guide for light detection 40$b$. The light detector 30 generates a light detection signal S1 showing the light intensity of light detected, etc. The thus generated light detection signal S1 is input to the signal processing unit 50. In addition to a photomultiplier tube (PMT), various substances such as a photodiode, an avalanche photodiode and a PIN photodiode may be used as the light detector 30. The light detector 30 may be selected from those having spectral sensitivity characteristics capable of sufficiently detecting light such as pulse light with a wavelength that is used in measuring a scattering medium. Further, when a light signal is subtle, it is preferable to use a light detector high in sensitivity or gain. The above-described light detector 30 and the light guide for light detection 40$b$ compose light detecting means for detecting pulse light made incident by the light incident means and transmitted inside a scattering medium SM at the light detecting position B to acquire a light detection signal.

The above-described light guide for light incidence 40$a$ and the light guide for light detection 40$b$ are not necessarily one respectively. For example, in an apparatus 10 for measuring a scattering medium which is used for diagnosis of breast cancer, a plurality of holders are installed on a cup-like gantry capable of accommodating a breast, that is, a scattering medium SM which is a measurement object. The light guides 40$a$, 40$b$ are inserted into each of these holders. It is desirable that those inserted into the holder are given as a light guide in which the incident light guide 40$a$ and the light guide 40$b$ for light detection are integrated into one piece, thus making it possible to either make light incident or detect the light at a position of any holder by control from the operation processing unit 60, etc.

The signal processing unit 50 is electrically connected to the light detector 30 and the light source 20. The signal processing unit 50 is signal processing means for acquiring a measurement waveform which shows temporal change in light intensity on the basis of a light detection signal detected by the light detector 30, a trigger signal S2 of pulse light emitted from the light source 20, etc. The information of the measurement waveform is acquired as electronic data D1 and input into the operation processing unit 60.

As shown in FIG. 2, the signal processing unit 50 is configured with a constant fraction discriminator (CFD) 51, a time-to-amplitude converter (TAC) 52 and an analog-to-digital converter (A/D) 53. The light detection signal which is an output signal from the light detector (PMT) 30 is guided into the TAC 50 via the CFD 51, converted to analog voltage corresponding to time and further converted to a digital signal by the analog-to-digital converter 53. This digital signal is to correspond to the data of measurement waveforms which show temporal change in detected light intensity.

In the apparatus 10 for measuring a scattering medium of the present embodiment, a scattering medium SM which is a measurement object and a scattering medium SM for reference are measured for each of the measurement waveforms showing temporal change in light intensity of pulse light after the pulse light is made incident, as will be described later. The scattering medium SM for reference is measured in order to eliminate the influence of an instrumental function from the measurement waveform of the scattering medium SM which is the measurement object. As the scattering medium SM for reference, a substance which is approximately equal in refractive index to the scattering medium SM which is the measurement object and also in which optical parameters necessary for calculating a theoretical waveform such as an absorption coefficient and a scattering coefficient are known is used.

The operation processing unit 60 is electrically connected to the signal processing unit 50 and accepts the input of information of a measurement waveform from the signal processing unit 50, thereby conducting operation processing for calculating the internal information of the scattering medium SM by using the information of the measurement waveform. In order to conduct the operation processing, as shown in FIG. 1, the operation processing unit 60 is provided as composed with a waveform processing unit 61, a measurement waveform storing unit 62, a theoretical waveform storing unit 63, and an internal information calculation unit 64. Further, it is desirable that the operation processing unit 60 also has functions to control the above-described configuration such as the light source 20 and the light detector 30.

The waveform processing unit 61 is waveform processing means for acquiring the waveform of the scattering medium SM which is the measurement object in which the influence of an instrumental function is eliminated on the basis of the measurement waveform acquired by the signal processing unit 50. That is, the waveform processing unit 61 is means for acquiring the theoretical waveform of the scattering medium SM which is the measurement object. The waveform processing unit 61 is that in which a theoretical waveform $P_m^{theory}$ (t) of a scattering medium SM which is a measurement object is shown by a previously available function with a predetermined parameter. The waveform processing unit 61 stores the function in advance. Here, the above-described t is elapsed time in which a time point when pulse light is made incident on the scattering medium SM (≈a time point when pulse light is emitted from the light source 20) is given as an original point (t=0), and a function value of $P_m^{theory}$ (t) shows light intensity at each of the time points.

In order to acquire a waveform of a scattering medium SM which is a measurement object from which the influence of an instrumental function is eliminated, the waveform processing unit 61 conducts operation processing in such a manner that the result of convolution operation on the theoretical waveform of the scattering medium SM which is the measurement object and the measurement waveform of the scattering medium SM for reference is made equal to the result of convolution operation on the theoretical waveform of the scattering medium SM for reference and the measurement waveform of the scattering medium SM which is the measurement object. That is, the waveform processing unit 61 is that in which when the measurement waveform of the scattering medium SM which is the measurement object is given as $P_m$ (t), the measurement waveform of the scattering medium SM for reference is given as $P_r$ (t), the theoretical waveform of the previously available scattering medium SM for reference is given as $P_r^{theory}$ (t) and convolution is given as an operator "*", the above parameters are specified so that the following formula;

$$P_r(t) * P_m^{theory}(t) = P_m(t) * P_r^{theory}(t)$$ [Mathematical formula 5]

can be met, thereby calculating the theoretical waveform $P_m^{theory}$ (t) of the scattering medium which is the measurement object. A function for showing the theoretical waveform of the scattering medium SM which is the measurement object and operation processing by the waveform processing unit 61 will be described later more specifically. The information of waveforms processed by the waveform processing unit 61 is output into the internal information calculation unit 64.

The measurement waveform storing unit 62 is to store the information of the measurement waveform of the scattering medium SM which is the measurement object acquired by the signal processing unit 50 and the measurement waveform of the scattering medium SM for reference (the above-described electronic data D1 input to the operation processing unit 60 from the signal processing unit 50). The information stored by the measurement waveform storing unit 62 is referenced whenever necessary in processing by the waveform processing unit 61.

The theoretical waveform storing unit 63 is to store the information of the theoretical waveform of the previously available scattering medium SM for reference. The theoretical waveform of the scattering medium SM for reference is calculated in advance, for example, by referring to optical parameters such as an absorption coefficient and a scattering coefficient of the scattering medium SM for reference. This calculation is carried out by, for example, a finite element method. In addition to this method, a Monte Carlo method, finite difference method and other analytic solution methods, etc., may be used. The information stored by the theoretical waveform storing unit 63 is referenced whenever necessary in processing by the waveform processing unit 61.

The internal information calculation unit 64 is internal information calculation means for calculating the internal information of a scattering medium SM which is a measurement object on the basis of the measurement waveform of the scattering medium SM which is the measurement object processed by the waveform processing unit 61. The internal information is calculated, for example, by applying analytical operation such as time resolved spectroscopy (TRS method) which utilizes a time-resolved waveform of detected light or phase modulation spectroscopy (PMS method) which utilizes modulated light, etc.

The operation processing unit 60 equipped with the above-described individual components is realized by, for example, a hardware configuration as shown in FIG. 2. In the operation processing unit 60, a central processing unit (CPU) 70 is electrically connected to the light source 20 and the signal processing unit 50. Thereby, timing of light detection in synchronization with incident light, etc., can be controlled by the CPU 70 and also the information of measurement waveforms output from the signal processing unit 50 is guided into the CPU 70 to conduct predetermined operation processing. Further, incident conditions of measured light such as the wavelength of incident pulse light are also controlled or selected by the CPU 70.

The operation processing unit 60 shown in FIG. 2 is additionally provided with a program memory 71 which stores an operating system (OS) 71a and an operation program 71b for conducting predetermined operation processing, a data file memory 72 for storing various types of data files, a data memory 73 for storing the information showing the internal information of an obtained scattering medium SM and a working memory 74 for temporarily storing working data.

The operation program 71b of the program memory 71 includes programs, etc., for carrying out the above-described waveform processing operation and analytical operation for calculating the internal information. Further, the data file memory 72 includes the measurement waveform storing unit 62 for storing the information of measurement waveforms and the theoretical waveform storing unit 63 for storing the information of the previously available theoretical waveform. Various data such as necessary physical quantities, data of previously input measurement conditions and known values, etc., are also stored.

Further, the operation processing unit 60 is provided with an input device 75 having a keyboard 75a and a mouse 75b for accepting input of data and an output device 76 having a display 76a and a printer 76b for outputting obtained data. Motions of individual parts of the operation processing unit 60 are all controlled by the CPU 70. The above-described individual memories may be a hard disk, etc., installed inside a computer. Still further, a specific hardware configuration of the apparatus 10 for measuring a scattering medium is not limited to that shown in FIG. 2 but may be modified or expanded whenever necessary.

Figure 3:
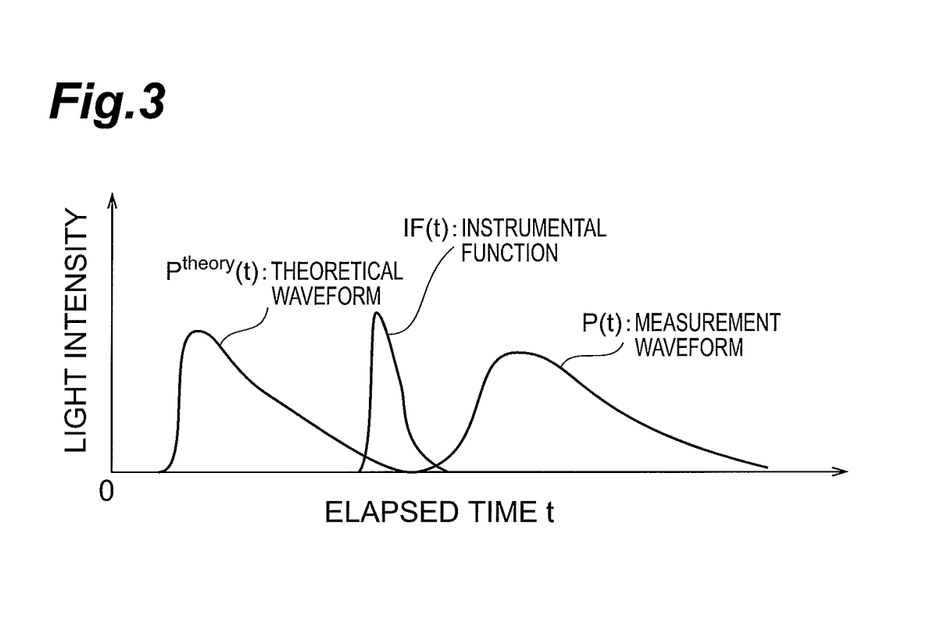
FIG. 3 is a graph which shows schematically one example of a measurement waveform, that of a theoretical waveform and that of an instrumental function.

Here, a description will be made for a relationship between a measurement waveform, a theoretical waveform with respect to a scattering medium and an instrumental function as well as operation processing by the waveform processing unit 61. FIG. 3 is a graph which shows schematically one example of a relationship between a measurement waveform $P(t)$, a theoretical waveform $P^{theory}(t)$ and an instrumental function $IF(t)$. In this graph, the horizontal axis shows elapsed time t in which a time point when pulse light is made incident on a scattering medium SM is given as an original point (t=0), whereas the vertical axis shows light intensity at each time point. Temporal change depending on the elapsed time t of light intensity gives individual time waveforms illustrated in the graph.

Pulse light is irradiated to a scattering medium SM which is a measurement object to obtain diffused light which is transmitted inside the scattering medium SM and emitted, and the thus obtained diffused light is ideally expressed by a theoretical waveform $P^{theory}(t)$. The internal information of the scattering medium should be calculated on the basis of this theoretical waveform $P^{theory}(t)$. However, on measurement of a scattering medium by the use of a measurement apparatus, in addition to response time by the scattering medium which is the measurement object, response time of the apparatus itself such as time delay or time dispersion as an instrumental function IF (t) resulting from individual parts and individual circuits of the measurement apparatus is generated. For example, in the apparatus 10 for measuring a scattering medium shown in FIG. 1, response time individually at the light source 20, the wavelength selector 21, the light detector 30, the light guides 40a, 40b and the signal processing unit 50 as well as at wirings, circuits, etc., between them is generated. The above-described response time is all given as an instrumental function expressing response time of the apparatus 10 for measuring a scattering medium itself. Therefore, a measurement waveform P (t) acquired by the signal processing unit 50 and input into the operation processing unit 60 is that in which the instrumental function IF (t) is convoluted to an ideal measurement waveform (theoretical waveform) $P^{theory}(t)$ of the scattering medium.

In response, in the apparatus 10 for measuring a scattering medium of the present embodiment, (the waveform processing unit 61) conducts operation processing in such a manner that the result of convolution operation on the theoretical waveform of the scattering medium SM which is the measurement object and the measurement waveform of the scattering medium SM for reference is made equal to the result of convolution operation on the theoretical waveform of the scattering medium SM for reference and the measurement waveform of the scattering medium SM which is the measurement object, thereby eliminating the influence of an instrumental function from the measurement waveform of the scattering medium SM which is the measurement object. More specifically, the following procedures will be conducted.

As described above, the measurement waveform of the scattering medium SM which is the measurement object is given as $P_m(t)$ and the measurement waveform of the scattering medium SM for reference is given as $P_r(t)$, and the respective theoretical waveforms are given as $P_m^{theory}(t)$ and $P_r^{theory}(t)$. Further, an instrumental function is given as IF (t). Here, the theoretical waveform $P_r^{theory}(t)$ of the scattering medium SM for reference is known for an optical coefficient of the scattering medium SM and therefore has been obtained in advance. The measurement waveform is that in which the instrumental function is convoluted to the theoretical waveform. Thus, a relationship shown by the following formulae (1) and (2) is obtained between individual waveforms.

[Mathematical formula 6]

$$P_r(t) = P_r^{theory}(t) * IF(t) \quad (1)$$

$$P_m(t) = P_m^{theory}(t) * IF(t) \quad (2)$$

These formulae are subjected to Fourier transformation to obtain the following formulae (3) and (4). However, Fourier transformation is expressed as F[•].

[Mathematical formula 7]

$$F[P_r(t)] = F[P_r^{theory}(t)] \cdot F[IF(t)] \quad (3)$$

$$F[P_m(t)] = F[P_m^{theory}(t)] \cdot F[IF(t)] \quad (4)$$

A relationship shown in the following formula (5) can be obtained from the formula (3) and the formula (4).

[Mathematical formula 8]

$$\frac{F[P_m(t)]}{F[P_r(t)]} = \frac{F[P_m^{theory}(t)] \cdot F[IF(t)]}{F[P_r^{theory}(t)] \cdot F[IF(t)]} = \frac{F[P_m^{theory}(t)]}{F[P_r^{theory}(t)]} \quad (5)$$

The formula (5) is transformed to obtain the following formula (6).

[Mathematical formula 9]

$$F[P_r(t)] \cdot F[P_m^{theory}(t)] = F[P_m(t)] \cdot F[P_r^{theory}(t)] \quad (6)$$

The formula (6) is subjected to Fourier inverse transformation to obtain the following formula (7).

[Mathematical formula 10]

$$P_r(t) * P_m^{theory}(t) = P_m(t) * P_r^{theory}(t) \quad (7)$$

The formula (7) expresses that the result of convolution operation on the theoretical waveform of the scattering medium SM which is the measurement object and the measurement waveform of the scattering medium SM for reference is made equal to the result of convolution operation on the theoretical waveform of the scattering medium SM for reference and the measurement waveform of the scattering medium SM which is the measurement object. Therefore, $P_m^{theory}(t)$ determined so as to meet the formula (7) is that in which the influence of the instrumental function is eliminated from the measurement waveform of the scattering medium SM which is the measurement object.

Here, the $P_m^{theory}(t)$ is handled as a previously available function which has t as a variable and also has a predetermined parameter. Determination of such a function that will meet the formula (7) by the waveform processing unit 61 is made by determining the above parameter. It is noted that a parameter to be determined which is included in the function showing the $P_m^{theory}(t)$ is not necessarily one but a plurality of parameters may be included as described later. More specifically, for example, a method of least squares is applied to determine parameters which will minimize the formula (8) shown below. Here, t is given as a discrete value $t_n$ (n=0, 1, ...) ($t_0$=0), and the parameters to be determined (a set thereof) is given as p.

[Mathemetical formula 11]

$$E(p) = \sum_{n=0}^{N-1} w(t_n)[s(p; t_n) - \tilde{s}(t_n)]^2 \quad (8)$$

In the formula (8),

[Mathematical formula 12]

$w(t)$: weighting function = $\frac{1}{\tilde{s}(t_n)}$ $\tilde{s}(t_n)$: $P_m(t) * P_r^{theory}(t)$ $s(p; t_n)$: $P_r(t) * P_m^{theory}(t)$ (term including the parameters to be determined).

Further, N in the formula (8) expresses a maximum value in a time range to be used in an analysis by the method of least squares and is a preset value. For example, where N is equal to 1024, analysis is made by using a value in a range of $t_0 \le t_n \le t_{1023}$. This time range is set so as to include the above-described individual theoretical waveforms and measurement waveforms. A reason for giving t as a discrete value is that usually, a waveform obtained by the signal processing unit 50 is a value of light intensity corresponding to a time point which is a digital value and may be considered as a continuous value.

As a function showing $P_m^{theory}(t_n)$, a function in which the above parameter is given to determine a waveform uniquely and light transmitted inside a scattering medium SM can be approximated (can be expressed) is used. More specifically, for example, parameters are given as A, α, β, (that is, a parameter p expressed in the form of a column vector is $$p = [A\alpha\beta]^T \quad \text{[Mathematical formula 13]}$$

(wherein T means a transposed matrix)), and as a function f (p; $t_n$) showing $P_m^{theory}(t_n)$, usable is the following formula (9).

[Mathematical formula 14]

$$P_m^{theory}(t_n) = f(p; t_n) = A \cdot t_n^{-\frac{5}{2}} \cdot \exp(-\alpha c t_n) \cdot \exp\left(-\frac{\gamma^2 + \kappa^2}{4\xi c t_n}\right) \quad (9)$$

Here, c is a value showing the speed of light, γ is a value showing a distance between a light incident position A and a light detecting position B, and they are information stored in advance as a set value at the waveform processing unit 61. Further,

[Mathematical formula 15]

$$\xi = \frac{1}{3\beta}, \kappa = \frac{1}{\beta}.$$

Temporal strength change (waveform) in light transmitted inside a scattering medium SM can be expressed approximately by such a function that is shown in the formula (9). Therefore, a function in the form of the formula (9) is appropriate in approximating $P_m^{theory}(t_n)$.

The formula (9) is that in which a following formula obtained analytically from a light diffusion equation as reflection light from a semi-infinite medium,

[Mathematical formula 16]

$$R(p; t_n) = (4\pi Dc)^{-\frac{3}{2}} z_0 \cdot t_n^{-\frac{5}{2}} \cdot \exp(-\mu_a c t_n) \cdot \exp\left(-\frac{\rho^2 + z_0^2}{4Dc t_n}\right)$$

is given as

[Mathematical formula 17]

$(4\pi Dc)^{-\frac{3}{2}} z_0 = A, \mu_a = \alpha, \mu_s' = \beta,$ $D = \xi = \frac{1}{3\beta}, \rho = \gamma, z_0 = \kappa = \frac{1}{\beta}.$ Here, R (p; $t_n$) is a value showing light intensity at a time point $t_n$ (p is a set of parameters in a formula analytically obtained from the above light diffusion equation), $\mu_a$ is a value showing an absorption coefficient of a scattering medium, D is a value showing a diffusion coefficient of the scattering medium (=⅓$\mu_s'$), $\mu_s'$ is a value showing a scattering coefficient of the scattering medium, ρ is a distance between a light incident position and a light detecting position, and c is a value showing the speed of light. In the present embodiment, since the formula (9) is also used where a waveform obtained in a scattering medium SM which is not in the form of a semi-infinite medium is to be analyzed, no physical meaning is found in each parameter of the formula (9).

As shown in the formula (9), a function whose waveform is determined by a predetermined parameter is used to approximate $P_m^{theory}(t)$, thus making it possible to determine a theoretical waveform free of the influence of noise contained in a measurement waveform. That is, where $P_m^{theory}(t_n)$ is not approximated by a function such as the formula (9) but determined directly (where a value itself of $P_m^{theory}(t_n)$ at each time point is determined), there is an influence by variance (noise) in measurement data at each time point. On the other hand, where the $P_m^{theory}(t_n)$ is approximated by the formula (9), parameters of A, α, β are given to determine uniquely a value of $P_m^{theory}(t_n)$ at each time point. Therefore, there is no influence by variance in measurement data at each time point.

As described above, it is desirable to use the formula (9) as a function which approximates $P_m^{theory}(t_n)$. However, this function is not limited to the formula (9). Any function may be used as long as it is that in which several predetermined parameters are given to determine a waveform uniquely and light transmitted inside a scattering medium SM can be approximated. Further, it is possible to use a waveform which is obtained by using numerical calculations such as a Monte Carlo method, a finite difference method and a finite element method.

Figure 4:
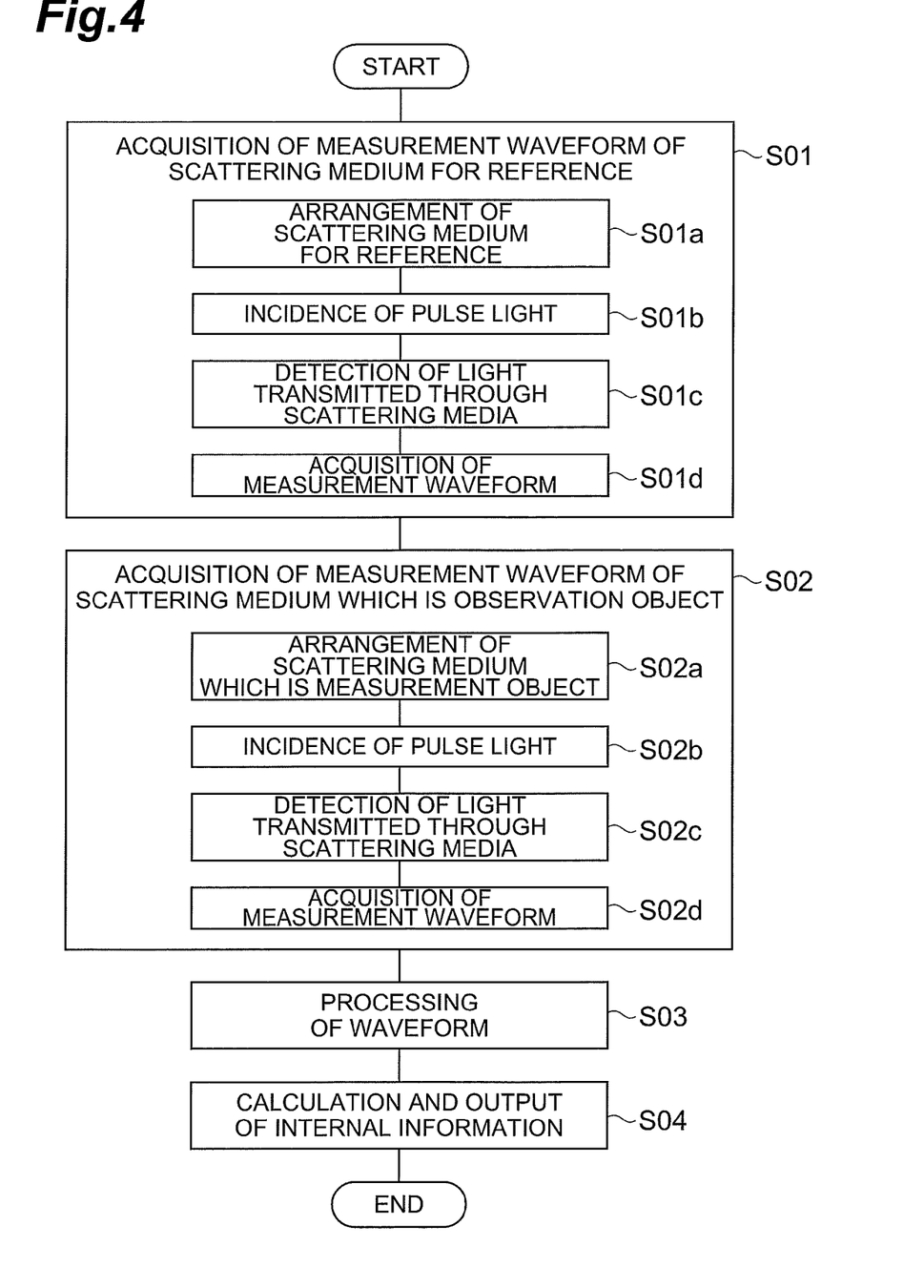
FIG. 4 is a flow chart which shows a method for measuring a scattering medium in an embodiment of the present invention.

Next, a description will be made by referring to the flow chart of FIG. 4 for the method for measuring a scattering medium in the present embodiment which is carried out by using the apparatus 10 for Measuring a scattering medium. The method for measuring a scattering medium is a method for measuring the internal information of a scattering medium SM which is a measurement object.

First, according to the method for measuring a scattering medium in the present embodiment, a measurement waveform $P_r(t)$ of a scattering medium SM for reference (S01) is acquired. The measurement waveform is specifically acquired as follows. First, the scattering medium SM for reference is arranged at a predetermined position of the apparatus 10 for measuring a scattering medium (S01a). This arrangement is made in such a manner that the apparatus 10 for measuring a scattering medium can be used to make pulse light incident on the scattering medium SM and detect light from the scattering medium SM. For example, where a gantry installed on the apparatus 10 for measuring a scattering medium is provided with a light incident position and a light detecting position, the gantry is filled with a scattering medium SM for reference. As described above, the theoretical waveform $P_r^{theory}(t)$ of the scattering medium SM for reference is calculated in advance and stored by the theoretical waveform storing unit 63.

Then, in the apparatus 10 for measuring a scattering medium, pulse light which is generated from the light source 20 and selected by the wavelength selector 21 according to a wavelength thereof passes through the light guide for light incidence 40a and is made incident on the scattering medium SM for reference from a predetermined light incident position (S01b, light incident step). The pulse light which has been made incident is scattered inside the scattering medium, absorbed and transmitted. In the apparatus 10 for measuring a scattering medium, the pulse light passes through the light guide 40b for light detection and is detected at a predetermined light detecting position by the light detector 30 (S01c, light detecting step). Further, a measurement waveform $P_r(t)$ showing temporal change in light intensity of the scattering medium SM for reference is acquired on the basis of the thus detected light detection signal by the signal processing unit 50 (S01d, signal processing step). The information of the acquired measurement waveform $P_r(t)$ is output to the operation processing unit 60 and stored by the measurement waveform storing unit 62.

Here, a position at which pulse light is made incident may be moved to several sites in such a manner that a light incident position is combined with a light detecting position to sufficiently acquire the internal information of the scattering medium SM, and the above steps (S01b to S01d) are repeated to acquire a plurality of measurement waveforms. Further, light may be detected at a plurality of light detecting positions for pulse light made incident from one site. For example, pulse light may be made incident from ten light incident positions at the gantry, by which the light is detected at 30 light detecting positions for one light incident position. In this instance, measurement waveforms of 10×30 are acquired.

Then, a measurement waveform $P_m(t)$ of a scattering medium SM which is a measurement object is acquired (S02). The measurement waveform $P_m(t)$ of the scattering medium SM which is the measurement object is acquired as follows. First, as with the measurement of the scattering medium SM for reference, the scattering medium SM which is the measurement object is arranged at a predetermined position of the apparatus 10 for measuring a scattering medium (S02a). For example, a breast, that is, a scattering medium SM which is a measurement object on a gantry provided on the apparatus 10 for measuring a scattering medium is arranged. Then, under the same conditions as those of the measurement of the scattering medium SM for reference, light is made incident, the light is detected and the measurement waveform, $P_m(t)$ is acquired the same as described above (S02b to S02d, light incident step, light detecting step and signal processing step). The information of the thus acquired measurement waveform, $P_m(t)$, is output to the operation processing unit 60 and stored by the measurement waveform storing unit 62. Acquisition of the measurement waveform $P_r(t)$ of the scattering medium SM for reference, (S01) and that of the measurement waveform $P_m(t)$ of the scattering medium SM which is the measurement object, (S02) may be performed in reverse order.

Then, the waveform processing unit 61 of the operation processing unit 60 can be used to acquire from the measurement waveform storing unit 62, the information which shows each of the measurement waveforms, $P_m(t)$ and $P_r(t)$ as well as the theoretical waveform $P_r^{theory}(t)$ of the scattering medium SM for reference. Further, the waveform processing unit 61 is used to read out a function showing a theoretical waveform $P_m^{theory}(t)$ having a parameter to be determined (which is stored by the waveform processing unit 61 itself). Then, as described above, the waveform processing unit 61 is used to conduct operation processing in such a manner that the result of convolution operation on the theoretical waveform $P_m^{theory}(t)$ of the scattering medium SM which is the measurement object and the measurement waveform $P_r(t)$ of the scattering medium SM for reference is made equal to the result of convolution operation on the theoretical waveform $P_r^{theory}(t)$ of the scattering medium SM for reference and the measurement waveform $P_m(t)$ of the scattering medium SM which is the measurement object. Thereby, a parameter of the theoretical waveform $P_m^{theory}(t)$ of the scattering medium SM which is the measurement object is calculated and specified. Thus, the parameter-specified theoretical waveform $P_m^{theory}(t)$ is that in which the influence of an instrumental function IF (t) is eliminated from the measurement waveform $P_m(t)$ (S03, waveform processing step). A response time waveform $P_m^{theory}(t)$ of the scattering medium SM which is the measurement object obtained by this processing (from which the influence of the instrumental function IF (t) is eliminated) is output to the internal information calculation unit 64.

Then, the internal information calculation unit 64 is used to calculate the internal information of the scattering medium SM which is the measurement object on the basis of a theoretical waveform $P_m^{theory}(t)$ of the scattering medium SM which is the measurement object shown by a function including the above-specified parameter (S04, internal information calculation step). The internal information to be calculated includes an absorption coefficient and a scattering coefficient, etc., of the scattering medium SM. The thus calculated internal information is distributed, for example, so as to be referenced by users, and output to the display 76a of the operation processing unit 60.

As described above, according to the method for measuring a scattering medium and the apparatus 10 for measuring a scattering medium in the present embodiment, on the basis of a relationship of the waveform shown by the formula (7), a parameter of a function showing a theoretical waveform $P_m^{theory}(t)$ of the scattering medium SM which is the measurement object is specified. Thereby, it is possible to obtain a theoretical waveform in which the influence of an instrumental function is eliminated from the measurement waveform of the scattering medium which is the measurement object, without using the instrumental function. That is, it is possible to calculate the internal information of the scattering medium SM which is the measurement object without using an instrumental function IF (t) on the basis of a waveform from which the influence of the instrumental function IF (t) is eliminated.

Further, the theoretical waveform $P_m^{theory}$ (t) of the scattering medium which is the measurement object is given as a previously available function with the above-described predetermined parameter, thus making it possible to prevent the influence of variance in measurement waveform. That is, even where noise is contained in a measurement waveform $P_m$ (t), it is possible to determine a theoretical waveform $P_m^{theory}$ (t) of the scattering medium SM which is the measurement object more accurately corresponding to $P_m$ (t). Therefore, according to the present invention, even where noise is contained in a measurement waveform $P_m$ (t), it is possible to acquire the internal information of the scattering medium more accurately and easily, with the influence of an instrumental function IF (t) taken into account.

Further, as described in the present embodiment, it is desirable that a function showing a theoretical waveform $P_m^{theory}$ (t) of the scattering medium SM which is the measurement object is given as that which shows more appropriately light transmitted inside the scattering medium, such as the formula (9). The above-described configuration is able to determine the theoretical waveform of the scattering medium which is the measurement object more accurately and, as a result, able to acquire the internal information of the scattering medium more accurately.

Figure 5:
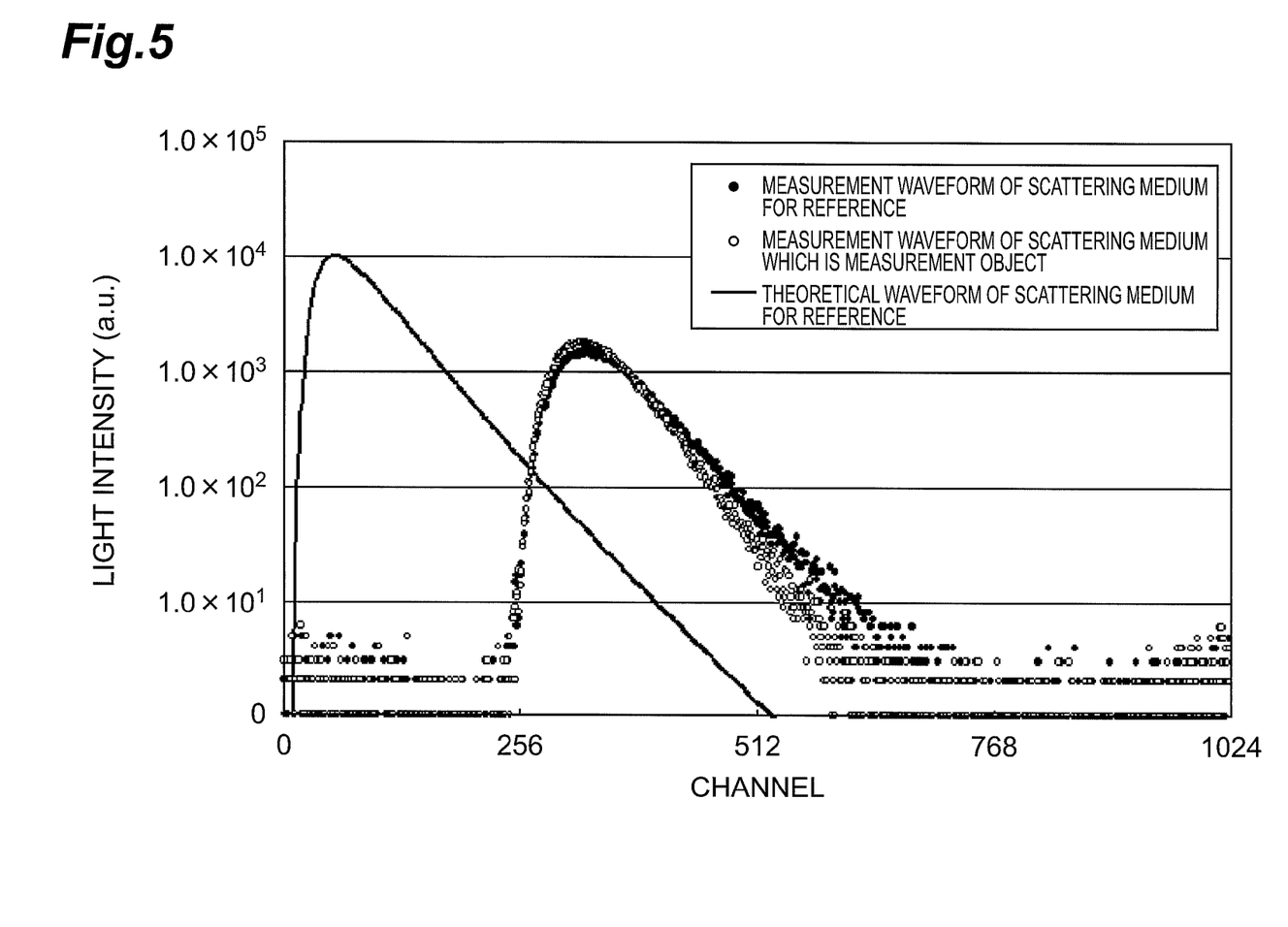
FIG. 5 is a graph which shows the respective examples of a measurement waveform of a scattering medium which is a measurement object, a measurement waveform of a scattering medium for reference and a theoretical waveform of the scattering medium for reference.

A description will be made by referring to FIG. 5 to FIG. 7 for an example which calculates a theoretical waveform $P_m^{theory}$ (t) of a scattering medium on the basis of the method of the present embodiment. FIG. 5 is a graph which shows a measurement waveform $P_m$ (t) of the scattering medium SM which is the measurement object, a measurement waveform $P_r$ (t) of the scattering medium SM for reference, and a theoretical waveform $P_r^{theory}$ (t) of the scattering medium SM for reference. In the graph of FIG. 5, the horizontal axis shows a channel (corresponding to elapsed time, time point), whereas the vertical axis shows light intensity (a. u.) (this is also applied to FIG. 6 and FIG. 7).

Figure 6:
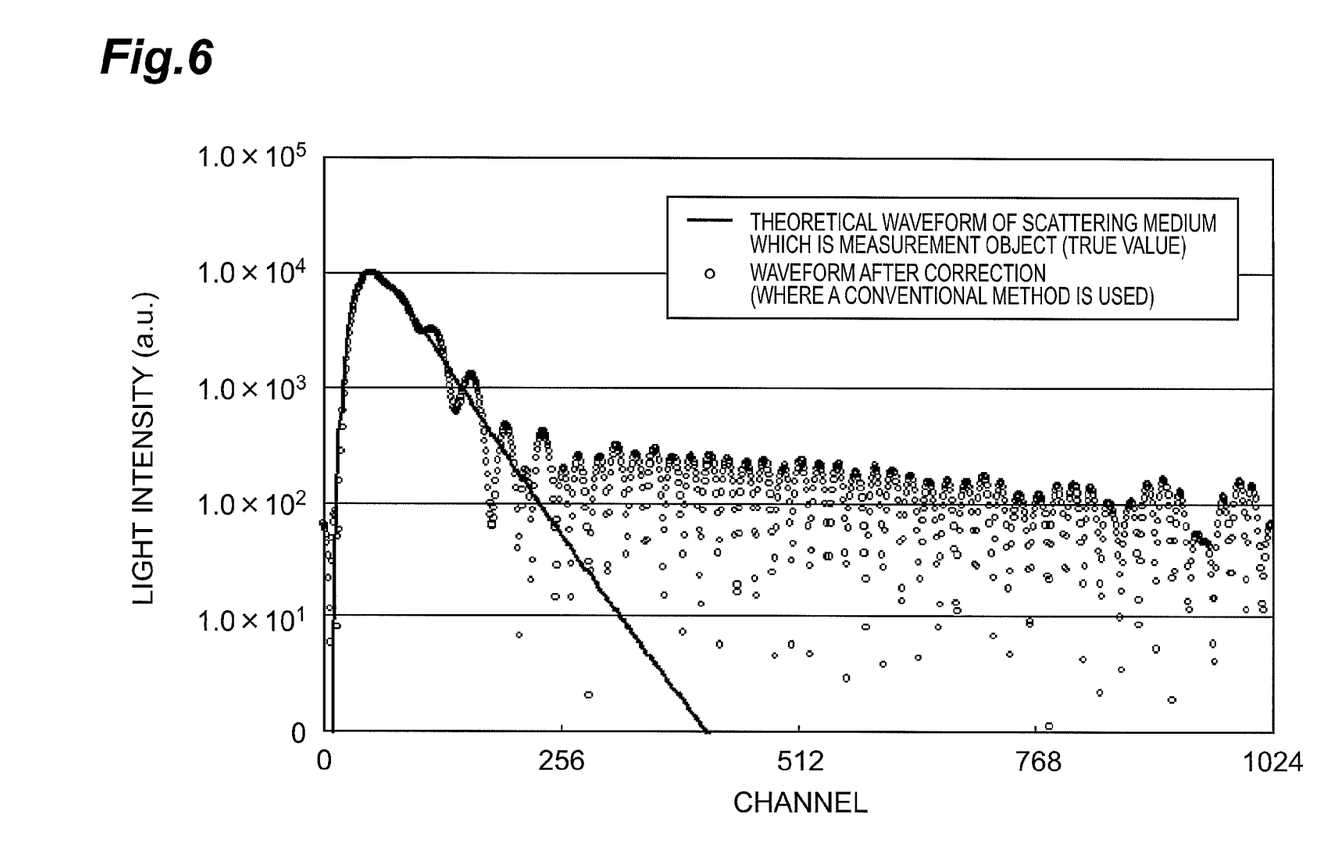
FIG. 6 is a graph which shows the respective examples of a theoretical waveform (true value) of a scattering medium which is a measurement object and a measurement waveform (calculated theoretical waveform) of the scattering medium which is the measurement object corrected by a conventional method.

FIG. 6 shows a theoretical waveform of the scattering medium SM which is the measurement object calculated by using the data shown in FIG. 5 according to the method described in Patent Literature 1 and an actual theoretical waveform (a true value). According to the method described in Patent Literature 1, since the operation of a waveform subjected to Fourier transformation is sensitive to noise contained in a measurement waveform, handling of the measurement waveform has been troublesome. Further, where the measurement waveform is used as it is to conduct the operation, there has been a case that due to the influence of noise, as shown in FIG. 6, the waveform after processing (calculated theoretical waveform) is greatly deviated from the true value and distorted.

Figure 7:
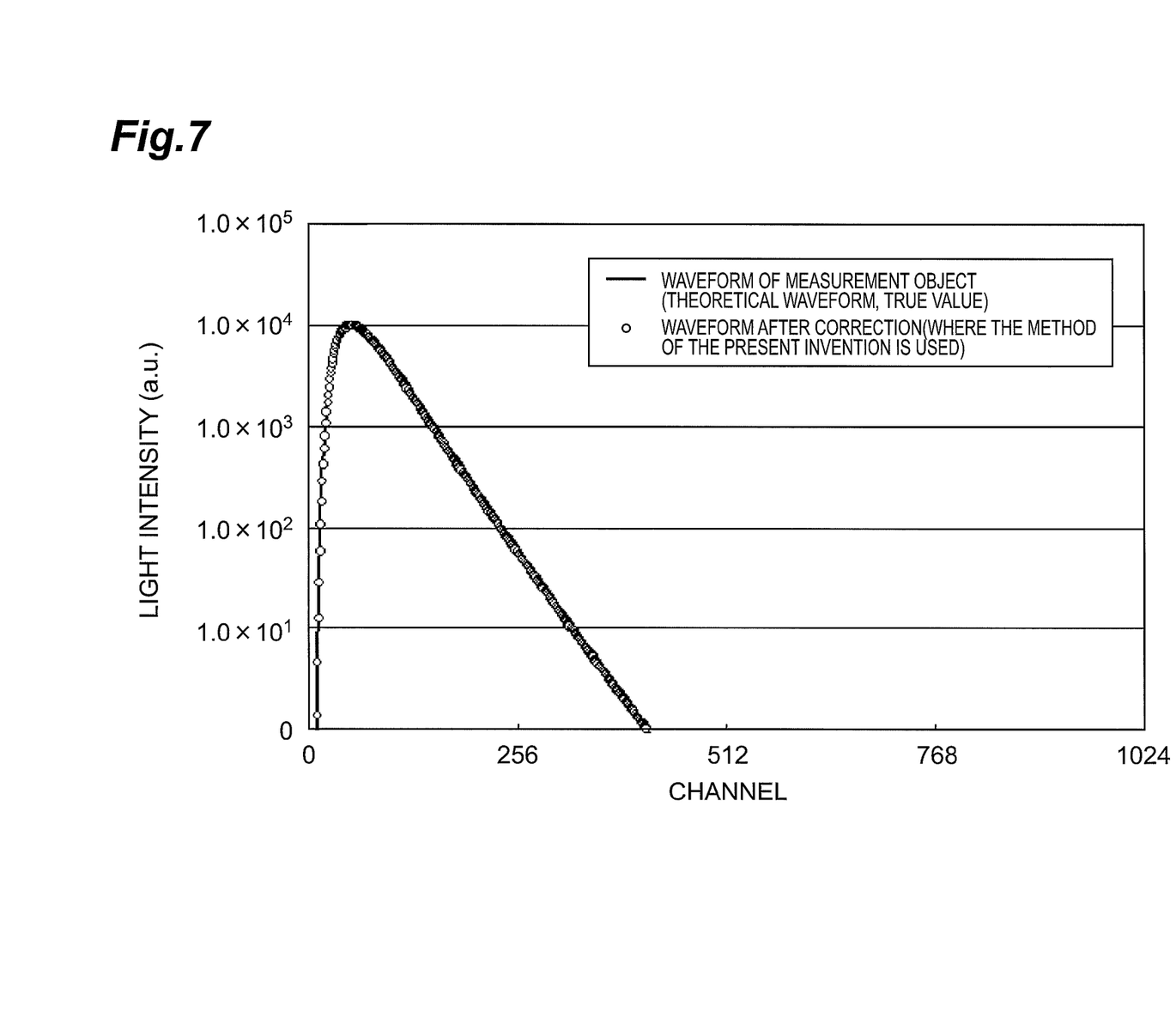
FIG. 7 is a graph which shows the respective examples of a theoretical waveform (true value) of a scattering medium which is a measurement object and a measurement waveform (calculated theoretical waveform) of the scattering medium which is the measurement object corrected by a method of the present invention.

FIG. 7 shows a theoretical waveform $P_m^{theory}$ (t) of the scattering medium SM which is the measurement object calculated by using the data shown in FIG. 5 according to the method of the present embodiment and an actual theoretical waveform (a true value). In the method of the present embodiment, the waveform after processing (calculated theoretical waveform) is substantially coincident with the true value. As apparent from this result, the method of the present embodiment is able to realize an accurate theoretical waveform even where noise is contained and, as a result, also able to acquire accurately the internal information of the scattering medium.

REFERENCE SIGNS LIST

10: apparatus for measuring a scattering medium, 20: light source, 21: wavelength selector, 30: light detector, 40a, 40b: light guide, 50: signal processing unit, 60: operation processing unit, 61: waveform processing unit, 62: measurement waveform storing unit, 63: theoretical waveform storing unit, 64: internal information calculation unit

The invention claimed is:

1. A method for measuring a scattering medium performed by an apparatus including a light detector, a signal processing unit, and a waveform processing unit, the method comprising:
a light incident step in which pulse light with a predetermined wavelength is made incident within a light incident arrangement from a light incident position to a scattering medium which is a measurement object and a scattering medium for reference;
a light detecting step in which the pulse light made incident in the light incident step and transmitted inside each of the scattering media is detected by the light detector at a light detecting position to acquire a light detection signal;
a signal processing step in which a measurement waveform showing temporal change in light intensity is acquired by the signal processing unit on the basis of the light detection signal detected by the light detector in the light detecting step;
a waveform processing step in which when the measurement waveform of the scattering medium which is the measurement object acquired by the signal processing unit in the signal processing step is given as $P_m$ (t), the theoretical waveform of the scattering medium which is the measurement object expressed by a previously available function having a predetermined parameter is given as $P_m^{theory}$ (t), the measurement waveform of the scattering medium for reference acquired in the signal processing step is given as $P_r$ (t), the theoretical waveform of the previously available scattering medium for reference is given as $P_r^{theory}$ (t), and convolution is given as an operator "*", the parameter is specified on the basis of the following formula:

$$P_r(t)*P_m^{theory}(t)=P_m(t)*P_r^{theory}(t);$$

and
an internal information calculation step in which on the basis of the theoretical waveform of the scattering medium which is the measurement object expressed by the function having the specified parameter in the waveform processing step, calculation is made by the waveform processing unit for the internal information of the scattering medium which is the measurement object.

2. The method for measuring a scattering medium according to claim 1, wherein the function showing $P_m^{theory}$ (t) is a discrete function of time point $t_n$ and when A, α, β are given as parameters, c is given as a value showing the speed of light and γ is given as a value showing a distance between the light incident position and the light detecting position, the function showing $P_m^{theory}$ (t) is expressed by the following formula:

$$P_m^{theory}(t_n) = A \cdot t_n^{-\frac{5}{2}} \cdot \exp(-\alpha c t_n) \cdot \exp\left(-\frac{\gamma^2 + \kappa^2}{4\xi c t_n}\right)$$

wherein $$\xi = \frac{1}{3\beta}, \kappa = \frac{1}{\beta}.$$

3. An apparatus for measuring a scattering medium comprising:
  light incident means in which pulse light with a predetermined wavelength is made incident from a light incident position to a scattering medium which is a measurement object and a scattering medium for reference;
  light detecting means in which the pulse light made incident by the light incident means and transmitted inside each of the scattering media is detected at a light detecting position to acquire a light detection signal;
  signal processing means in which a measurement waveform showing temporal change in light intensity is acquired on the basis of the light detection signal detected by the light detecting means;
  waveform processing means in which when the measurement waveform of the scattering medium which is the measurement object acquired by the signal processing means is given as $P_m(t)$, the theoretical waveform of the scattering medium which is the measurement object expressed by a previously available function having a predetermined parameter is given as $P_m^{theory}(t)$, the measurement waveform of the scattering medium for reference acquired by the signal processing means is given as $P_r(t)$, the theoretical waveform of the previously available scattering medium for reference is given as $P_r^{theory}(t)$ and convolution is given as an operator "*", the parameter is specified on the basis of the following formula:

$$P_r(t)*P_m^{theory}(t)=P_m(t)*P_r^{theory}(t);$$

and
  internal information calculation means in which on the basis of the theoretical waveform of the scattering medium which is the measurement object expressed by the function having the specified parameter by the waveform processing means, calculation is made for the internal information of the scattering medium which is the measurement object.

\* \* \* \* \*